United States Patent
Simpson et al.

(10) Patent No.: US 11,872,341 B2
(45) Date of Patent: Jan. 16, 2024

(54) VAPOR PROVISION CARTRIDGE AND SYSTEM

(71) Applicant: Nicoventures Trading Limited., London (GB)

(72) Inventors: Alexander Simpson, London (GB); Terry Lee Angell, London (GB)

(73) Assignee: NICOVENTURES TRADING LIMITED, London (GB)

( * ) Notice: Subject to any disclaimer, the term of this patent is extended or adjusted under 35 U.S.C. 154(b) by 671 days.

(21) Appl. No.: 15/733,231

(22) PCT Filed: Dec. 5, 2018

(86) PCT No.: PCT/GB2018/053520
§ 371 (c)(1),
(2) Date: Jun. 12, 2020

(87) PCT Pub. No.: WO2019/116004
PCT Pub. Date: Jun. 20, 2019

(65) Prior Publication Data
US 2020/0376210 A1     Dec. 3, 2020

(30) Foreign Application Priority Data
Dec. 14, 2017  (GB) ...................... 1720849

(51) Int. Cl.
*A61M 15/06*  (2006.01)
*A61M 11/04*  (2006.01)
(Continued)

(52) U.S. Cl.
CPC .............. *A61M 15/06* (2013.01); *A24F 40/10* (2020.01); *A24F 40/42* (2020.01); *A24F 40/44* (2020.01); *A24F 40/50* (2020.01); *A61M 11/042* (2014.02)

(58) Field of Classification Search
CPC .......... A24F 40/10; A24F 40/40; A24F 40/42; A24F 40/30; A61M 15/60; A61M 11/042
See application file for complete search history.

(56) References Cited

U.S. PATENT DOCUMENTS 9,901,122 B2 *   2/2018  Li ........................... A24F 40/46
10,188,146 B2 *  1/2019  Chen ....................... H05B 3/46
(Continued)

FOREIGN PATENT DOCUMENTS

CN     103300481 A    9/2013
CN     206443209 U    8/2017
(Continued)

OTHER PUBLICATIONS

International Preliminary Report on Patentability for Application No. PCT/GB2018/053520, dated Mar. 6, 2020, 6 pages.
(Continued)

*Primary Examiner* — Marcus E Harcum
(74) *Attorney, Agent, or Firm* — Patterson, Thuente PA (57) ABSTRACT

A cartridge for a vapor provision system including the cartridge and a control unit, wherein the cartridge includes a housing part having a mouthpiece end and an interface end, wherein the mouthpiece end includes a vapor outlet for the cartridge and the interface end includes an interface for coupling the cartridge to a control unit; an air channel extending from an air inlet in the housing part to the vapor outlet; a reservoir within the housing part containing liquid for vaporization, wherein an end of the reservoir at the interface end of the housing part is sealed by a resilient plug, wherein the reservoir includes a dividing wall between a first reservoir region on a side of the dividing wall facing the mouth piece end of the housing part and a second reservoir region on a side of the dividing wall facing the interface end of the housing part, wherein the dividing wall includes at least one fluid communication opening to provide fluid (Continued)

communication between the first reservoir region and the second reservoir region; and a liquid transport element arranged to transport liquid from the second region of the reservoir to a vaporizer for generating vapor in a vapor generation region for user inhalation.

14 Claims, 5 Drawing Sheets

(51) Int. Cl.
*A24F 40/10* (2020.01)
*A24F 40/44* (2020.01)
*A24F 40/42* (2020.01)
*A24F 40/50* (2020.01)

(56) References Cited

U.S. PATENT DOCUMENTS

| | | | | |
|---|---|---|---|---|
| 10,856,581 | B2* | 12/2020 | Qiu | A24F 40/40 |
| 10,874,147 | B2* | 12/2020 | Qiu | A24F 40/485 |
| 11,234,464 | B2* | 2/2022 | Qiu | A24F 40/485 |
| 11,246,349 | B2* | 2/2022 | Ouyang | A24F 40/485 |
| 11,259,573 | B2* | 3/2022 | Qiu | A24F 40/40 |
| 2012/0111347 | A1* | 5/2012 | Hon | A24F 40/40 |
| | | | | 131/329 |
| 2013/0228191 | A1* | 9/2013 | Newton | A61M 15/06 |
| | | | | 131/329 |
| 2014/0109921 | A1* | 4/2014 | Chen | A24F 40/44 |
| | | | | 131/273 |
| 2014/0150783 | A1* | 6/2014 | Liu | A24F 40/40 |
| | | | | 128/202.21 |
| 2014/0196717 | A1* | 7/2014 | Liu | A24F 40/44 |
| | | | | 128/202.21 |
| 2014/0334803 | A1* | 11/2014 | Li | A61M 15/06 |
| | | | | 392/394 |
| 2014/0360514 | A1* | 12/2014 | Zhu | A24F 40/42 |
| | | | | 131/329 |
| 2015/0059787 | A1* | 3/2015 | Qiu | H05B 3/14 |
| | | | | 392/395 |
| 2015/0157053 | A1* | 6/2015 | Mayor | A24F 40/485 |
| | | | | 131/329 |
| 2015/0282529 | A1* | 10/2015 | Li | A61M 11/042 |
| | | | | 131/273 |
| 2015/0305408 | A1* | 10/2015 | Liu | H05B 3/06 |
| | | | | 392/404 |
| 2015/0313288 | A1* | 11/2015 | Liu | A24F 40/49 |
| | | | | 131/329 |
| 2016/0007654 | A1* | 1/2016 | Zhu | A24F 40/42 |
| | | | | 131/328 |
| 2016/0073692 | A1* | 3/2016 | Alarcon | A24F 40/44 |
| | | | | 131/329 |
| 2016/0183596 | A1* | 6/2016 | Rado | F22B 1/284 |
| | | | | 392/404 |
| 2017/0020193 | A1 | 1/2017 | Davis et al. | |
| 2017/0347705 | A1* | 12/2017 | Li | A61M 15/0023 |
| 2018/0020730 | A1* | 1/2018 | Alarcon | A24F 40/42 |
| | | | | 131/329 |
| 2018/0049470 | A1* | 2/2018 | Chen | H05B 3/46 |
| 2018/0177233 | A1* | 6/2018 | Tucker | A24F 40/30 |
| 2018/0213845 | A1* | 8/2018 | Qiu | A24F 40/485 |
| 2019/0082739 | A1* | 3/2019 | Slivestrini | A24F 40/485 |
| 2019/0166907 | A1* | 6/2019 | Chung | A24F 40/485 |
| 2019/0166913 | A1* | 6/2019 | Trzecieski | A61M 15/06 |
| 2021/0127742 | A1* | 5/2021 | Kim | A61M 15/06 |

FOREIGN PATENT DOCUMENTS

| | | |
|---|---|---|
| WO | 2016004576 A1 | 1/2016 |
| WO | 2016090426 A1 | 6/2016 |
| WO | 2016172023 A1 | 10/2016 |
| WO | 2017163046 A1 | 9/2017 |

OTHER PUBLICATIONS

International Search Report and Written Opinion for Application No. PCT/GB2018/053520, dated Feb. 25, 2019, 10 pages.

* cited by examiner

VAPOR PROVISION CARTRIDGE AND SYSTEM

PRIORITY CLAIM

The present application is a National Phase entry of PCT Application No. PCT/GB2018/053520, filed Dec. 5, 2018, which claims priority from Great Britain Application No. 1720849.7, filed Dec. 14, 2017, each of which is hereby fully incorporated herein by reference.

TECHNICAL FIELD

The present disclosure relates to vapor provision systems such as nicotine delivery systems (e.g. electronic cigarettes and the like).

BACKGROUND

Electronic vapor provision systems such as electronic cigarettes (e-cigarettes) generally contain a vapor precursor material, such as a reservoir of a source liquid containing a formulation, typically including nicotine, or a solid material such a tobacco-based product, from which a vapor is generated for inhalation by a user, for example through heat vaporization. Thus, a vapor provision system will typically comprise a vaporizer, e.g. a heating element, arranged to vaporize a portion of precursor material to generate a vapor in a vapor generation region of an air channel through the vapor provision system. As a user inhales on the device and electrical power is supplied to the vaporizer, air is drawn into the device through one or more inlet holes and along the air channel to the vaporizer generation region, where the air mixes with the vaporized precursor material and forms a condensation aerosol. The air drawn through the vaporizer generation region continues along the air channel to a mouthpiece opening, carrying some of the aerosol with it, and out through the mouthpiece opening for inhalation by the user.

It is common for vapor provision systems to comprise a modular assembly, often having two main functional parts, namely a control unit and disposable/replaceable cartridge part. Typically the cartridge part will comprise the consumable vapor precursor material and the vaporizer (atomizer), while the control unit part will comprise longer-life items, such as a rechargeable battery, device control circuitry, activation sensors and user interface features. The control unit may also be referred to as a reusable part or battery section and the replaceable cartridge may also be referred to as a disposable part or cartomizer.

The control unit and cartridge are mechanically coupled together at an interface for use, for example using a screw thread, bayonet, latched or friction fit fixing. When the vapor precursor material in a cartridge has been exhausted, or the user wishes to switch to a different cartridge having a different vapor precursor material, the cartridge may be removed from the control unit and a replacement cartridge may be attached to the device in its place.

A potential drawbacks for cartridges containing liquid vapor precursor (e-liquid) is the risk of leakage. An e-cigarette cartridge will typically have a mechanism, e.g. a capillary wick, for drawing liquid from a liquid reservoir to a vaporizer located in an air path/channel connecting from an air inlet to a vapor outlet for the cartridge. Because there is a fluid transport path from the liquid reservoir into the open air channel through the cartridge, there is a corresponding risk of liquid leaking from the cartridge. Leakage is undesirable both from the perspective of the end user naturally not wanting to get the e-liquid on their hands or other items, and also from a reliability perspective, since leakage from an end of the cartridge connected to the control unit may damage the control unit, for example due to corrosion. Some approaches to reduce the risk of leakage may involve restricting the flow of liquid to the vaporizer, for example by tightly clamping a wick where it enters the air channel, but this can in some scenarios lead to a risk of insufficient liquid being supplied to the vaporizer (dry-out), which can give rise to overheating and undesirable flavors.

Various approaches are described herein which seek to help address or mitigate some of the issues discussed above.

SUMMARY

According to a first aspect of certain embodiments there is provided a cartridge for a vapor provision system comprising the cartridge and a control unit, wherein the cartridge comprises: a housing part having a mouthpiece end and an interface end, wherein the mouthpiece end includes a vapor outlet for the cartridge and the interface end includes an interface for coupling the cartridge to a control unit; an air channel extending from an air inlet in the housing part to the vapor outlet; a reservoir within the housing part containing liquid for vaporization, wherein an end of the reservoir at the interface end of the housing part is sealed by a resilient plug, wherein the reservoir includes a dividing wall between a first reservoir region on a side of the dividing wall facing the mouth piece end of the housing part and a second reservoir region on a side of the dividing wall facing the interface end of the housing part, wherein the dividing wall comprises at least one fluid communication opening to provide fluid communication between the first reservoir region and the second reservoir region; and a liquid transport element arranged to transport liquid from the second region of the reservoir to a vaporizer for generating vapor in a vapor generation region for user inhalation.

According to a second aspect of certain embodiments there is provided a vapor provision system comprising the cartridge of the above-mentioned first aspect of certain embodiments and a control unit, wherein the control unit comprises a cartridge receiving section that includes an interface arranged to cooperatively engage with the interface at the interface end of the cartridge so as to releasably couple the cartridge to the control unit, wherein the control unit further comprises a power supply and control circuitry configured to selective supply power from the power supply to the vaporizer in the cartridge via their cooperatively engaging interfaces.

According to a third aspect of certain embodiments there is provided a cartridge means for vapor provision system means comprising the cartridge means and a control unit means, wherein the cartridge means comprises: a housing part means having a mouthpiece end means and an interface end means, wherein the mouthpiece end means includes a vapor outlet means for the cartridge means and the interface end means includes an interface means for coupling the cartridge means to a control unit means; an air channel means extending from an air inlet means in the housing part means to the vapor outlet means; a reservoir means within the housing part containing liquid for vaporization, wherein an end of the reservoir means at the interface end means of the housing part means is sealed by a resilient plug means, wherein the reservoir means includes a dividing wall means between a first reservoir region on a side of the dividing wall means facing the mouth piece end means of the housing part means and a second reservoir region on a side of the dividing wall means facing the interface end means of the housing part means, wherein the dividing wall means comprises at least one fluid communication opening means to provide fluid communication between the first reservoir region and the second reservoir region; and a liquid transport element means arranged to transport liquid from the second region of the reservoir to a vaporizer means for generating vapor in a vapor generation region for user inhalation.

It will be appreciated that features and aspects of the disclosure described above in relation to the various aspects of the disclosure are equally applicable to, and may be combined with, embodiments of the disclosure according to other aspects of the disclosure as appropriate, and not just in the specific combinations described herein.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to vapor provision systems, which may also be referred to as aerosol provision systems, such as e-cigarettes. Throughout the following description the term "e-cigarette" or "electronic cigarette" may sometimes be used, but it will be appreciated this term may be used interchangeably with vapor provision system/device and electronic vapor provision system/device. Furthermore, and as is common in the technical field, the terms "vapor" and "aerosol", and related terms such as "vaporize" and "aerosolize", may generally be used interchangeably.

As noted above, vapor provision systems (e-cigarettes) often comprise a modular assembly including both a reusable part (control unit) and a replaceable (disposable) cartridge part. Devices conforming to this type of two-part modular configuration may generally be referred to as two-part devices. It is also common for electronic cigarettes to have a generally elongate shape. For the sake of providing a concrete example, certain embodiments of the disclosure described herein comprise this kind of generally elongate two-part device employing disposable cartridges. However, it will be appreciated the underlying principles described herein may equally be adopted for other electronic cigarette configurations, for example modular devices comprising more than two parts, as devices conforming to other overall shapes, for example based on so-called box-mod high performance devices that typically have a more boxy shape.

Figure 1:
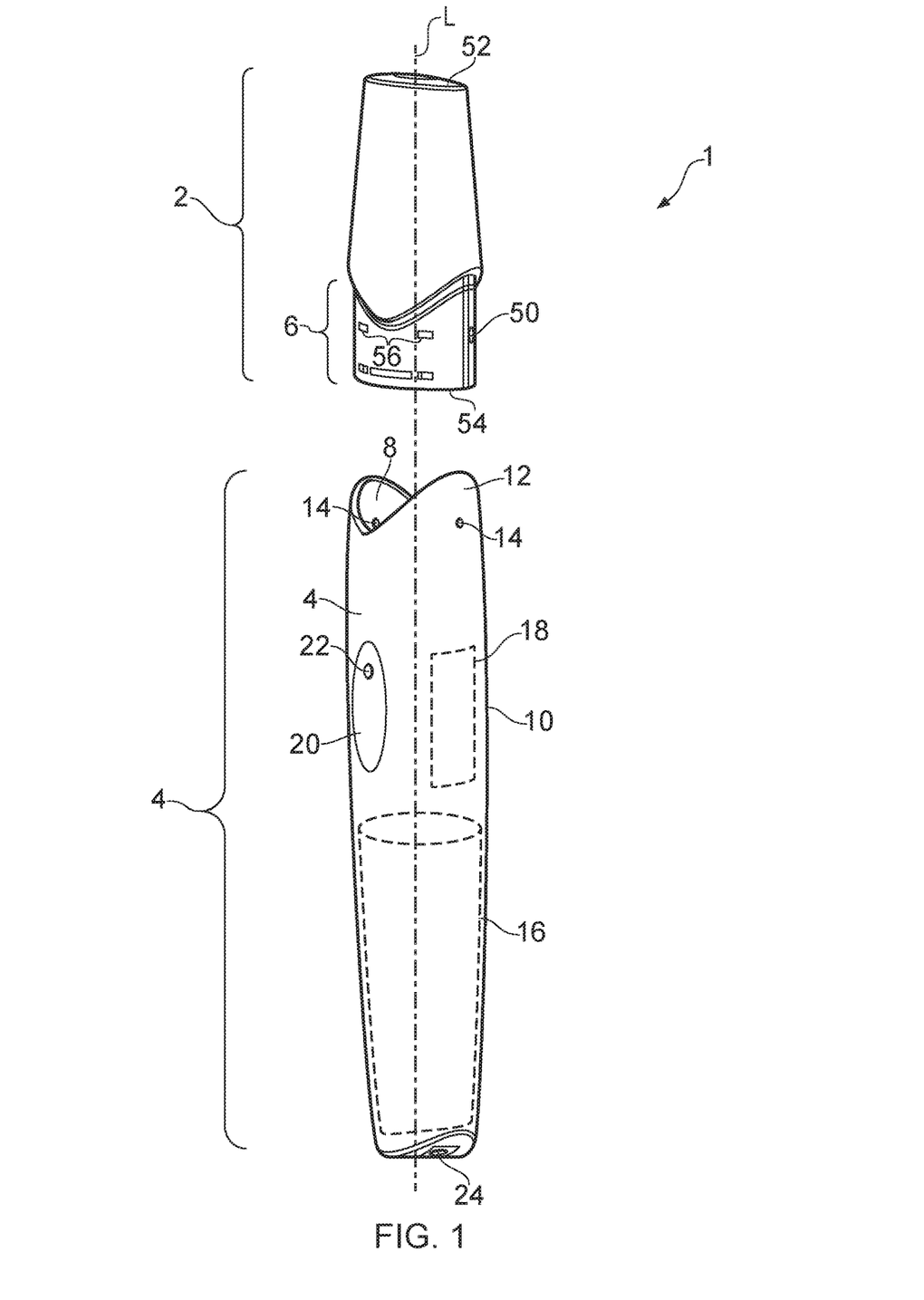
FIG. 1 schematically represents in perspective view a vapor provision system comprising a cartridge and control unit (shown separated) in accordance with certain embodiments of the disclosure.

FIG. 1 is a schematic perspective view of an example vapor provision system/device (e-cigarette) 1 in accordance with certain embodiments of the disclosure. Terms concerning the relative location of various aspects of the electronic cigarette (e.g. terms such as upper, lower, above, below, top, bottom etc.) are used herein with reference to the orientation of the electronic cigarette as shown in FIG. 1 (unless the context indicates otherwise). However, it will be appreciated this is purely for ease of explanation and is not intended to indicate there is any required orientation for the electronic cigarette in use.

The e-cigarette 1 comprises two main components, namely a cartridge 2 and a control unit 4. The control unit 4 and the cartridge 2 are shown separated in FIG. 1, but are coupled together when in use.

The cartridge 2 and control unit 4 are coupled by establishing a mechanical and electrical connection between them. The specific manner in which the mechanical and electrical connection is established is not of primary significance to the principles described herein and may be established in accordance with conventional techniques, for example based around a screw thread, bayonet, latched or friction-fit mechanical fixing with appropriately arranged electrical contacts/electrodes for establishing the electrical connection between the two parts as appropriate. For the example electronic cigarette 1 represented in FIG. 1, the cartridge comprises a mouthpiece end 52 and an interface end 54 and is coupled to the control unit by inserting an interface end portion 6 at the interface end of the cartridge into a corresponding receptacle 8/receiving section of the control unit. The interface end portion 6 of the cartridge is a close fit to be receptacle 8 and includes protrusions 56 which engage with corresponding detents in the interior surface of a receptacle wall 12 defining the receptacle 8 to provide a releasable mechanical engagement between the cartridge and the control unit. An electrical connection is established between the control unit and the cartridge via a pair of electrical contacts on the bottom of the cartridge (not shown in FIG. 1) and corresponding sprung contact pins in the base of the receptacle 8 (not shown in FIG. 1). As noted above, the specific manner in which the electrical connection is established is not significant to the principles described herein, and indeed some implementations might not have an electrical connection between the cartridge and a control unit at all, for example because the transfer of electrical power from the reusable part to the cartridge may be wireless (e.g. based on electromagnetic induction techniques).

The electronic cigarette 1 has a generally elongate shape extending along a longitudinal axis L. When the cartridge is coupled to the control unit, the overall length of the electronic cigarette in this example (along the longitudinal axis) is around 12.5 cm. The overall length of the control unit is around 9 cm and the overall length of the cartridge is around 5 cm (i.e. there is around 1.5 cm of overlap between the interface end portion 6 of the cartridge and the receptacle 8 of the control unit when they are coupled together). The electronic cigarette has a cross-section which is generally oval and which is largest around the middle of the electronic cigarette and tapers in a curved manner towards the ends. The cross-section around the middle of the electronic cigarette has a width of around 2.5 cm and a thickness of around 1.7 cm. The end of the cartridge has a width of around 2 cm and a thickness of around 0.6 mm, whereas the other end of the electronic cigarette has a width of around 2 cm and a thickness of around 1.2 cm. The outer housing of the electronic cigarette is in this example is formed from plastic. It will be appreciated the specific size and shape of the electronic cigarette and the material from which it is made is not of primary significance to the principles described herein and may be different in different implementations. That is to say, the principles described herein may equally be adopted for electronic cigarettes having different sizes, shapes and/or materials.

The control unit 4 may in accordance with certain embodiments of the disclosure be broadly conventional in terms of its functionality and general construction techniques. In the example of FIG. 1, the control unit 4 comprises a plastic outer housing 10 including the receptacle wall 12 that defines the receptacle 8 for receiving the end of the cartridge as noted above. The outer housing 10 of the control unit 4 in this example has a generally oval cross section conforming to the shape and size of the cartridge 2 at their interface to provide a smooth transition between the two parts. The receptacle 8 and the end portion 6 of the cartridge 2 are symmetric when rotated through 180° so the cartridge can be inserted into the control unit in two different orientations. The receptacle wall 12 includes two control unit air inlet openings 14 (i.e. holes in the wall). These openings 14 are positioned to align with an air inlet 50 for the cartridge when the cartridge is coupled to the control unit. A different one of the openings 14 aligns with the air inlet 50 of the cartridge in the different orientations. It will be appreciated some implementations may not have any degree of rotational symmetry such that the cartridge is couplable to the control unit in only one orientation while other implementations may have a higher degree of rotational symmetry such that the cartridge is couplable to the control unit in more orientations.

The control unit further comprises a battery 16 for providing operating power for the electronic cigarette, control circuitry 18 for controlling and monitoring the operation of the electronic cigarette, a user input button 20, an indicator light 22, and a charging port 24.

The battery 16 in this example is rechargeable and may be of a conventional type, for example of the kind normally used in electronic cigarettes and other applications requiring provision of relatively high currents over relatively short periods. The battery 16 may be recharged through the charging port 24, which may, for example, comprise a USB connector.

The input button 20 in this example is a conventional mechanical button, for example comprising a sprung mounted component which may be pressed by a user to establish an electrical contact in underlying circuitry. In this regard, the input button may be considered an input device for detecting user input, e.g. to trigger vapor generation, and the specific manner in which the button is implemented is not significant. For example, other forms of mechanical button or touch-sensitive button (e.g. based on capacitive or optical sensing techniques) may be used in other implementations, or there may be no button and the device may rely on a puff detector for triggering yap vapor our generation.

The indicator light 22 is provided to give a user with a visual indication of various characteristics associated with the electronic cigarette, for example, an indication of an operating state (e.g. on/off/standby), and other characteristics, such as battery life or fault conditions. Different characteristics may, for example, be indicated through different colors and/or different flash sequences in accordance with generally conventional techniques.

The control circuitry 18 is suitably configured/programmed to control the operation of the electronic cigarette to provide conventional operating functions in line with the established techniques for controlling electronic cigarettes. The control circuitry (processor circuitry) 18 may be considered to logically comprise various sub-units/circuitry elements associated with different aspects of the electronic cigarette's operation. For example, depending on the functionality provided in different implementations, the control circuitry 18 may comprises power supply control circuitry for controlling the supply of power from the battery to the cartridge in response to user input, user programming circuitry for establishing configuration settings (e.g. user-defined power settings) in response to user input, as well as other functional units/circuitry associated functionality in accordance with the principles described herein and conventional operating aspects of electronic cigarettes, such as indicator light display driving circuitry and user input detection circuitry. It will be appreciated the functionality of the control circuitry 18 can be provided in various different ways, for example using one or more suitably programmed programmable computer(s) and/or one or more suitably configured application-specific integrated circuit(s)/circuitry/chip(s)/chipset(s) configured to provide the desired functionality.

Figure 2:
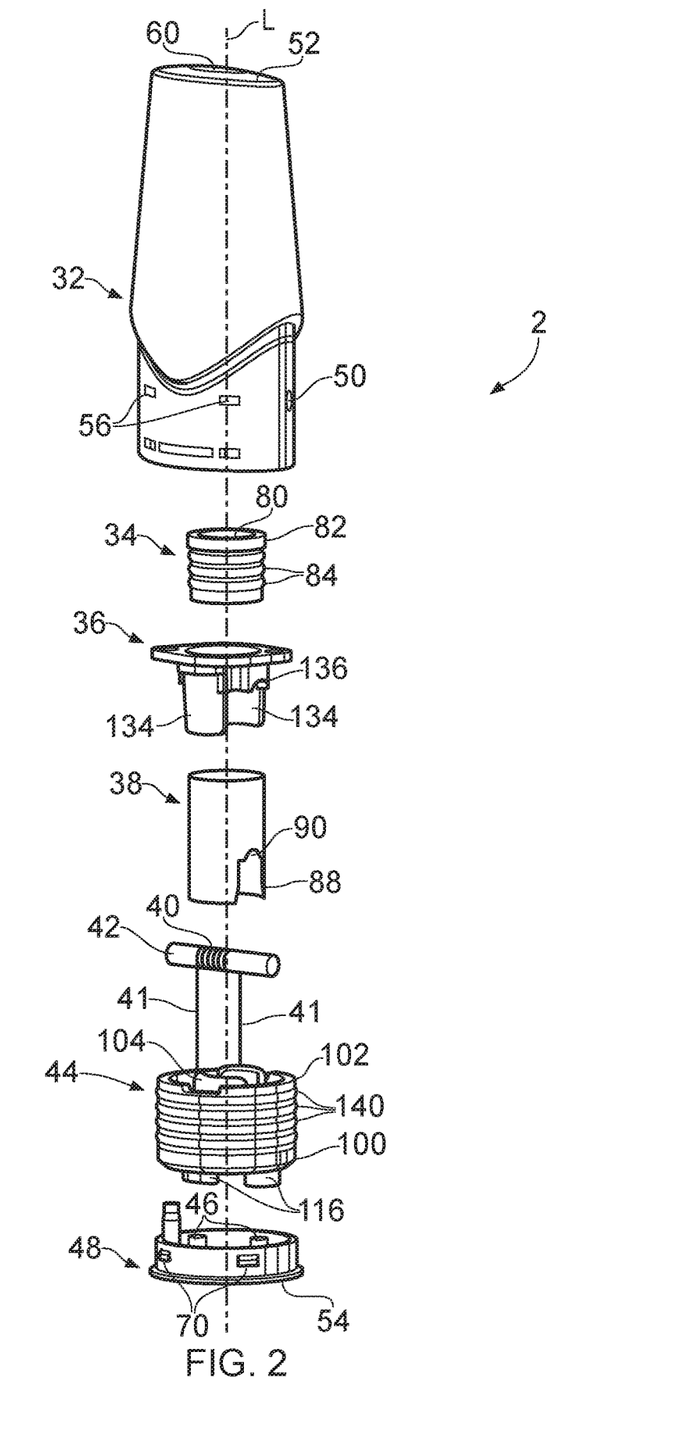
FIG. 2 schematically represents in exploded perspective view of components of the cartridge of the vapor provision system of FIG. 1.

FIG. 2 is an exploded schematic perspective view of the cartridge 2 (exploded along the longitudinal axis L). The cartridge 2 comprises a housing part 32, an air channel seal 34, a dividing wall element 36, an outlet tube 38, a vaporizer 40, a liquid transport element 42, a resilient plug 44, and an end cap 48 with contact electrodes 46. FIGS. 3 to 6 schematically represents some of these components in more detail.

Figure 3A:
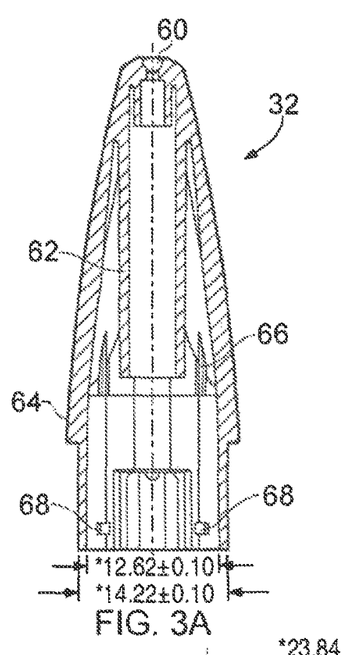
FIGS. 3A to 3C schematically represent various cross-section views of a housing part of the cartridge of the vapor provision system of FIG. 1.
Figure 3B:
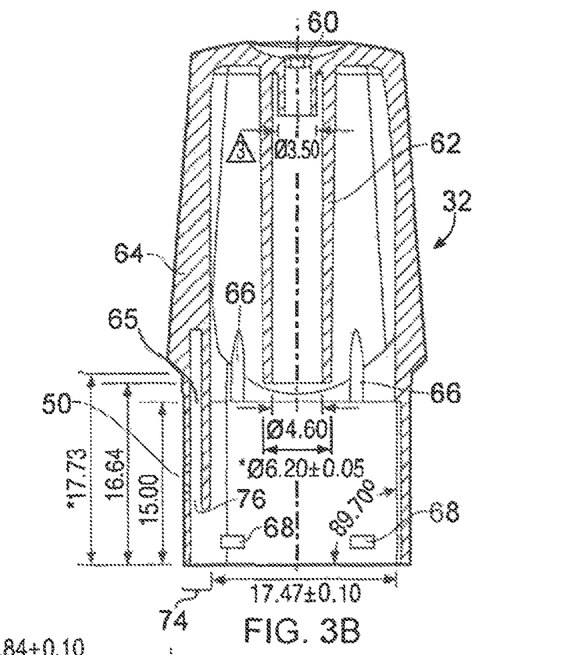
Figures 3C, 4A, 4B:
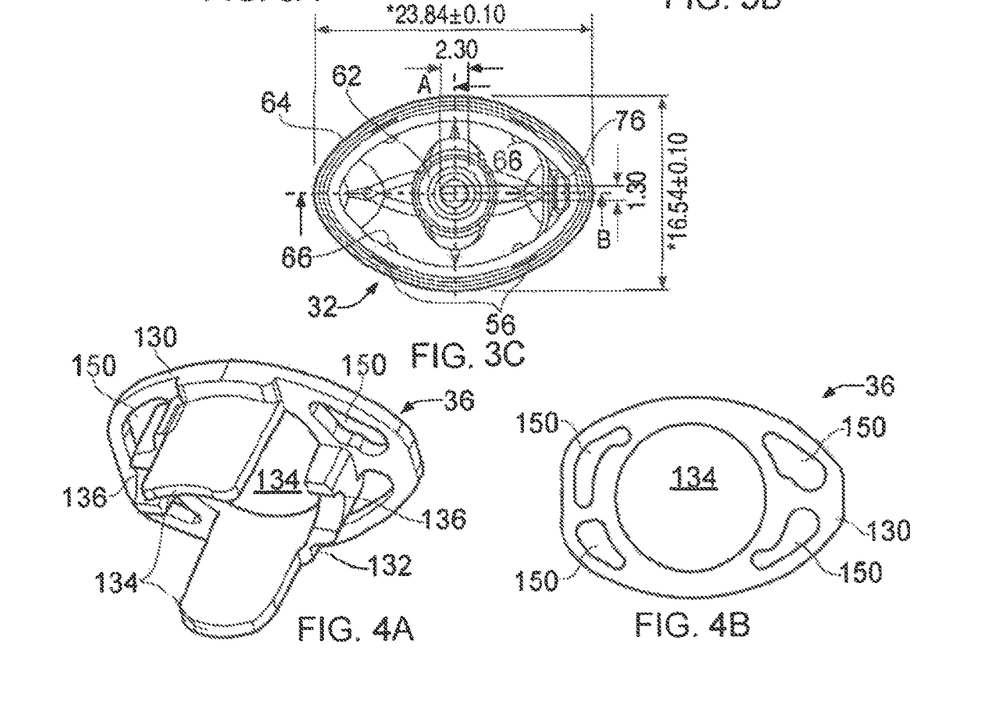
FIGS. 4A and 4B schematically represent a perspective view and a plan view of a dividing wall element of the cartridge of the vapor provision system of FIG. 1.

FIG. 3A is a schematic cut-away view of the housing part 32 through the longitudinal axis L where the housing part 32 is thinnest. FIG. 3B is a schematic cut-away view of the housing part 32 through the longitudinal axis L where the housing part 32 is widest. FIG. 3C is a schematic view of the housing part along the longitudinal axis L from the interface end 54 (i.e. viewed from below in the orientation of FIGS. 3A and 3B).

FIG. 4A is a schematic perspective view of the dividing wall element 36 as seen from below. FIG. 4B is a schematic cross-section through an upper part of the dividing wall element 36 as viewed from below.

Figure 5A:
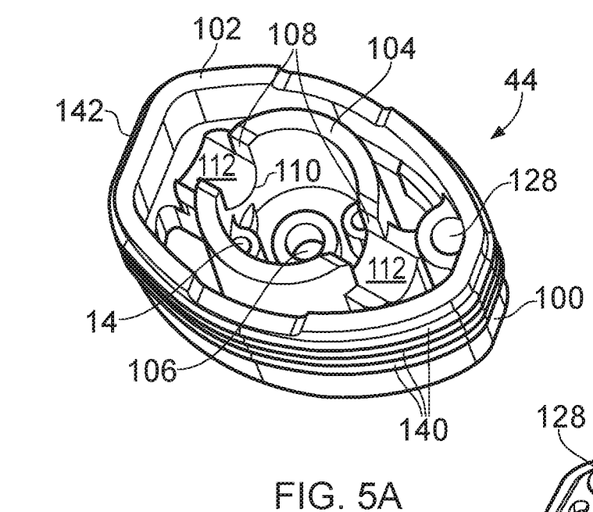
FIGS. 5A to 5C schematically represent two perspective views and a plan view of a resilient plug of the cartridge of the vapor provision system of FIG. 1.
Figure 5B:
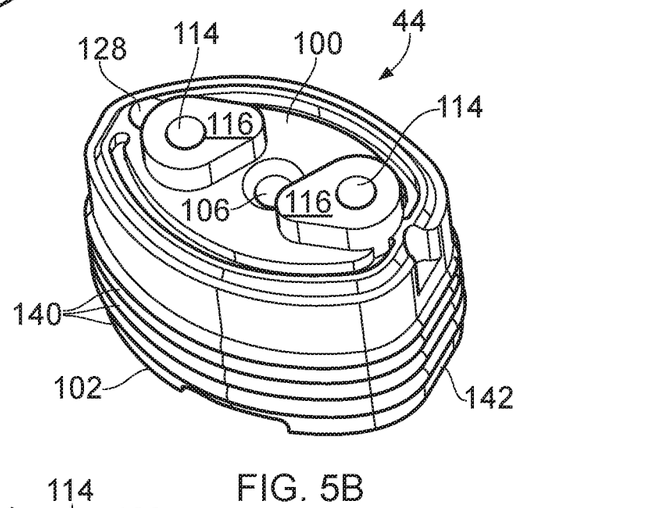
Figure 5C:
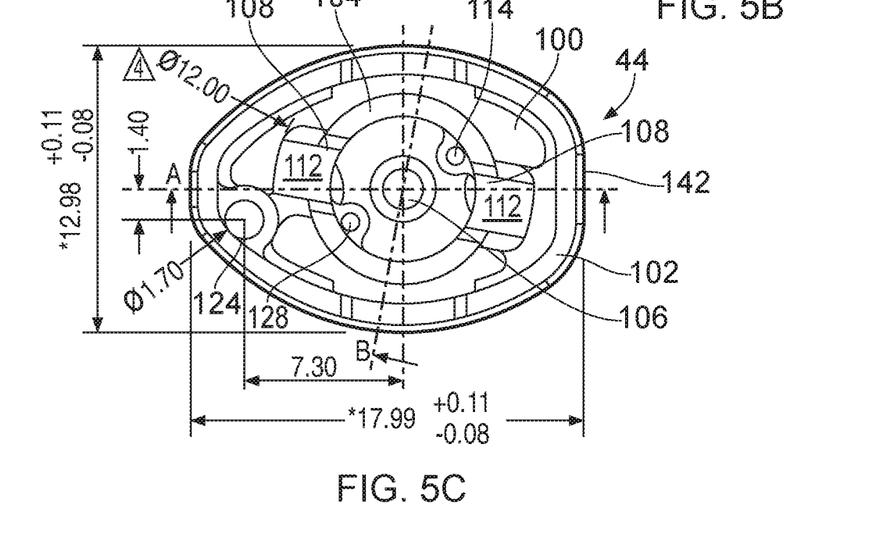

FIG. 5A is a schematic perspective view of the resilient plug 44 from above and FIG. 5B is a schematic perspective view of the resilient plug 44 from below. FIG. 5C is a schematic view of the resilient plug 44 along the longitudinal axis L seen from the mouthpiece end 52 of the cartridge (i.e. viewed from above for the orientation in FIGS. 1 and 2).

Figure 6A:
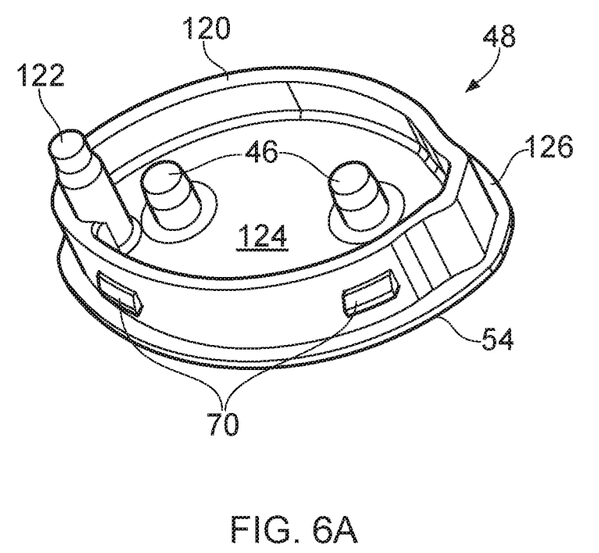
FIGS. 6A and 6B schematically represent a perspective view and a plan view of a bottom cap of the cartridge of the vapor provision system of FIG. 1.
Figure 6B:
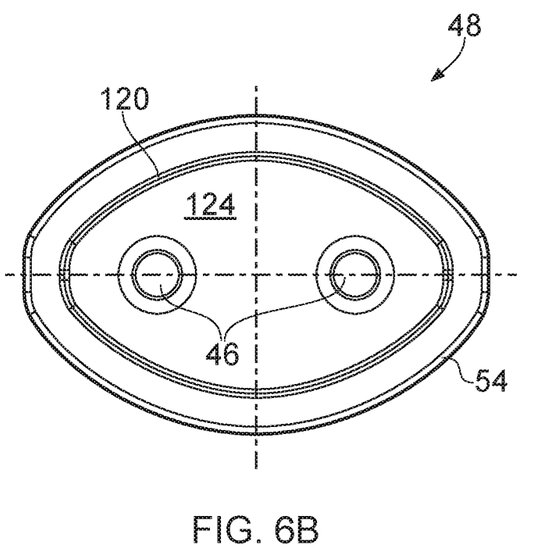

FIG. 6A is a schematic perspective view of the end cap 48 from above. FIG. 6B is a schematic view of the end cap 48 along the longitudinal axis L seen from the mouthpiece end 52 of the cartridge (i.e. from above).

The housing part 32 in this example comprises a housing outer wall 64 and a housing inner tube 62 which in this example are formed from a single molding of polypropylene. The housing outer wall 64 defines the external appearance of the cartridge 2 and the housing inner tube 62 defines a part of an air channel 65 through the cartridge. The housing part is open at the interface end 54 of the cartridge and closed at the mouthpiece end 52 of the cartridge except for a mouthpiece opening/vapor outlet 60 in fluid communication with the housing inner tube 62. The housing part 32 includes an opening in a sidewall which provides the air inlet 50 for the cartridge. The air inlet 50 in this example has an area of around 2 mm². The outer surface of the outer wall 64 of the housing part 32 includes the protrusions 56 discussed above which engage with corresponding detents in the interior surface of the receptacle wall 12 defining the receptacle 8 to provide a releasable mechanical engagement between the cartridge and the control unit. The inner surface of the outer wall 64 of the housing part includes further protrusions 66 which act to provide an abutment stop for locating the dividing wall element 36 along the longitudinal axis L when the cartridge is assembled. The outer wall 64 of the housing part 32 further comprises holes which provide latch recesses 68 arranged to receive corresponding latch projections 70 in the end cap to fix the end cap to be housing part when the cartridge is assembled.

The outer wall 64 of the housing part 32 includes a double-walled section 74 that defines a gap 76 in fluid communication with the air inlet 50. The gap 76 provides a portion of the air channel 65 through the cartridge. In this example the doubled-walled section 74 of the housing part 32 is arranged so the gap defines the air channel 65 running within the housing outer wall 64 parallel to the longitudinal axis with a cross-section in a plane perpendicular to the longitudinal axis of around 3 mm². The gap 76 of air channel 65 defined by the double-walled section of the housing part extends down to the open end of the housing part 32.

The air channel seal 34 is a silicone molding generally in the form of a tube having a through hole 80. The outer wall of the air channel seal 34 includes circumferential ridges 84 and an upper collar 82. The inner wall of the air channel seal 34 also includes circumferential ridges, but these are not visible in FIG. 2. When the cartridge is assembled the air channel seal 34 is mounted to the housing inner tube 62 with an end of the housing inner tube 62 extending partly into the through hole 80 of the air channel seal 34. The through hole 80 in the air channel seal has a diameter of around 5.8 mm in its relaxed state whereas the end of the housing inner tube 62 has a diameter of around 6.2 mm so that a seal is formed when the air channel seal 34 is stretched to accommodate the housing inner tube 62. This seal is facilitated by the ridges on the inner surface of the air channel seal 34.

The outlet tube 38 comprises a tubular section of ANSI 304 stainless steel with an internal diameter of around 8.6 mm and a wall thickness of around 0.2 mm. The bottom end of the outlet tube 38 includes a pair of diametrically opposing slots 88 with an end of each slot having a semi-circular recess 90. When the cartridge is assembled the outlet tube 38 mounts to the outer surface of the air channel seal 34. The outer diameter of the air channel seal is around 9.0 mm in its relaxed state so that a seal is formed when the air channel seal 34 is compressed to fit inside the outlet tube 38. This seal is facilitated by the ridges 84 on the outer surface of the air channel seal 34. The collar 80 on the air channel seal 34 provides a stop for the outlet tube 38.

The liquid transport element 42 comprises a capillary wick and the vaporizer 40 comprises a resistance wire heater wound around the capillary wick. In addition to the portion of the resistance wire wound around the capillary wick, the vaporizer 40 comprises electrical leads 41 which pass through holes in the resilient plug 44 to contact electrodes 46 mounted to the end cap 54 to allow power to be supplied to the vaporizer 40 via the electrical interface established when the cartridge is connected to a control unit. The electrical leads 41 may comprise the same material as the resistance wire wound around the capillary wick, or may comprise a different material (e.g. lower-resistance material) connected to the resistance wire wound around the capillary wick. In this example the heater coil 40 comprises a nickel iron alloy wire and the wick 42 comprises a glass fiber bundle. The vaporizer 40 and liquid transport element 42 may be provided in accordance with any conventional techniques and is may comprise different forms and/or different materials. For example, in some implementations the wick may comprise fibrous or solid a ceramic material and the heater may comprise a different alloy. In other examples the heater and wick may be combined, for example in the form of a porous and a resistive material. More generally, it will be appreciated the specific nature liquid transport element and vaporizer is not of primary significance to the principles described herein.

When the cartridge is assembled, the wick 42 is received in the semi-circular recesses 90 of the outlet tube 38 so that a central portion of the wick about which the heating coil is wound is inside the outlet tube while end portions of the wick are outside the outlet tube 38.

The resilient plug 44 in this example comprises a single molding of silicone. The resilient plug comprises a base part 100 with an outer wall 102 extending upwardly therefrom (i.e. towards the mouthpiece end of the cartridge). The resilient plug further comprises an inner wall 104 extending upwardly from the base part 100 and surrounding a through hole 106 through the base part 100.

The outer wall 102 of the resilient plug 44 conforms to an inner surface of the housing part 32 so that when the cartridge is assembled the resilient plug in 44 forms a seal with the housing part 32. The inner wall 104 of the resilient plug 44 conforms to an inner surface of the outlet tube 38 so that when the cartridge is assembled the resilient plug 44 also forms a seal with the outlet tube 38. The inner wall 104 includes a pair of diametrically opposing slots 108 with the end of each slot having a semi-circular recess 110. Extended outwardly (i.e. in a direction away from the longitudinal axis of the cartridge) from the bottom of each slot in the inner wall 104 is a cradle section 112 shaped to receive a section of the liquid transport element 42 when the cartridge is assembled. The slots 108 and semi-circular recesses 110 provided by the inner wall of the resilient plug 44 and the slots 88 and semi-circular recesses 90 of the outlet tube 38 are aligned so that the slots 88 in the outlet tube 38 accommodate respective ones of the cradles 112 with the respective semi-circular recesses in the outlet tube and resilient plug cooperating to define holes through which the liquid transport element passes. The size of the holes provided by the semi-circular recesses through which the liquid transport element passes correspond closely to the size and shape of the liquid transport element, but are slightly smaller so a degree of compression is provided by the resilience of the resilient plug 44. This allows liquid to be transported along the liquid transport element 42 by capillary action while restricting the extent to which liquid which is not transported by capillary action can pass through the openings. As noted above, the resilient plug 44 includes further openings 114 in the base part 100 through which the contact leads 41 for the vaporizer 40 pass when the cartridge is assembled. The bottom of the base part of the resilient plug includes spacers 116 which maintain an offset between the remaining surface of the bottom of the base part and the end cap 48. These spacers 116 include the openings 114 through which the electrical contact leads 41 for the vaporizer 40 pass.

The end cap 48 comprises a polypropylene molding with a pair of gold-plated copper electrode posts 46 mounted therein.

The ends of the electrode posts 46 on the bottom side of the end cap 48 are close to flush with the interface end 54 of the cartridge provided by the end cap 48. These are the parts of the electrodes to which correspondingly aligned sprung contacts in the control unit connect when the cartridge is assembled and connected to the control unit. The ends of the electrode posts on the inside of the cartridge extend away from the end cap 48 and into the holes 114 in the resilient plug 44 through which the contact leads 41 pass. The electrode posts are slightly oversized relative to the holes 114 and include a chamfer at their upper ends to facilitate insertion into the holes 114 in the resilient plug 44 where they are maintained in pressed contact with the contact leads for the vaporizer 40 by virtue of the resilient nature of the resilient plug 44.

The end cap has a base section 124 and an upstanding wall 120 which conforms to the inner surface of the housing part 32. The upstanding wall 120 of the end cap 48 is inserted into the housing part 32 so the latch projections 70 engage with the latch recesses 68 in the housing part 32 to snap-fit the end cap 48 to the housing part when the cartridge is assembled. The top of the upstanding wall 120 of the end cap 48 abuts a peripheral part of the resilient plug 44 and the lower face of the spacers 116 on the resilient plug also abut the base section 124 of the resilient plug so that when the end cap 48 is attached to the housing part it presses against the resilient part 44 to maintain it in slight compression.

The base portion 124 of the end cap 48 includes a peripheral lip 126 beyond the base of the upstanding wall 112 with a thickness which corresponds with the thickness of the outer wall of the housing part at the interface end of the cartridge. The end cap also includes an upstanding locating pin 122 which aligns with a corresponding locating hole 128 in the resilient plug to help establish their relative location during assembly.

The dividing wall element 36 comprises a single molding of polypropylene and includes a dividing wall 130 and a collar 132 formed by projections from the dividing wall 130 in the direction towards the interface end of the cartridge. The dividing wall element 36 has a central opening 134 through which the outlet tube 38 passes (i.e. the dividing wall is arranged around the outlet tube 38). When the cartridge is assembled, the upper surface of the outer wall 102 of the resilient plug 44 engages with the lower surface of the dividing wall 130, and the upper surface of the dividing wall 130 in turn engages with the projections 66 on the inner surface of the outer wall 64 of the housing part 32. Thus, the dividing wall 130 prevents the resilient plug from being pushed too far into the housing part 32—i.e. the dividing wall 130 is fixedly located along the longitudinal axis of the cartridge by the protrusions 66 in the housing part and so provides the resilient plug with a fixed surface to push against. The collar 132 formed by projections from the dividing wall includes a first pair of opposing projections/tongues 134 which engage with corresponding recesses on an inner surface of the outer wall 102 of the resilient plug 44. The protrusions from the dividing wall 130 further provide a pair of cradle sections 136 configured to engage with corresponding ones of the cradle sections 112 in the resilient part 44 when the cartridge is assembled to further define the opening through which the liquid transport element passes.

When the cartridge is assembled the air channel 65 extending from the air inlet 50 to the vapor outlet 60 through the cartridge is formed. Starting from the air inlet 50 in the side wall of the housing part 32, a first section of the air channel 65 is provided by the gap 76 formed by the double-walled section 74 in the outer wall 64 of the housing part 32 and extends from the air inlet 50 towards the interface end 54 of the cartridge and past the resilient plug 44. A second portion of the air channel 65 is provided by the gap between the base of the resilient plug 44 and the end cap 48. A third portion of the air channel 65 is provided by the hole 106 through the resilient plug 44. A fourth portion of the air channel 65 is provided by the region within the inner wall 104 of the resilient plug and the outlet tube around the vaporizer 40. This fourth portion of the air channel 65 may also be referred to as a vapor generation region, it being the primary region in which vapor is generated during use. The air channel 65 from the air inlet 50 to the vapor generation region may be referred to as an air inlet section of the air channel 65. A fifth portion of the air channel 65 is provided by the remainder of the outlet tube 38. A sixth portion of the air channel 65 is provided by the outer housing inner tube 62 which connects the air channel 65 to the vapor outlet 60. The air channel 65 from the vapor generation region to be the vapor outlet may be referred to as a vapor outlet section of the air channel 65.

Also, when the cartridge is assembled a reservoir for liquid is formed by the space outside the air channel 65 and inside the housing part 32. This may be filled during manufacture, for example through a filling hole which is then sealed, or by other means. The specific nature of the liquid, for example in terms of its composition, is not of primary significance to the principles described herein, and in general any conventional liquid of the type normally used in electronic cigarettes may be used. The reservoir is closed at the interface end of the cartridge by the resilient plug 44. The reservoir includes a first region above the dividing wall 130 and a second region below the dividing wall 130 within the space formed between the air channel 65 and the outer wall of the resilient plug. The liquid transport element (capillary wick) 42 passes through openings in the wall of the air channel provided by the semi-circular recesses 110, 90 in the resilient plug 44 and the outlet tube 38 and the cradle sections 112, 136 in the resilient plug 44 and the dividing wall element 36 that engage with one another as discussed above. Thus, the ends of the liquid transport element extend into the second region of the reservoir from which they draw liquid through the openings in the air channel 65 to the vaporizer 40 for subsequent vaporization.

In normal use, the cartridge 2 is coupled to the control unit 4 and the control unit activated to supply power to the cartridge via the contact electrodes 46 in the end cap 48. Power then passes through the connection leads 41 to the vaporizer 40. The vaporizer 40 is thus electrically heated and so vaporizes a portion of the liquid from the liquid transport element in the vicinity of the vaporizer 40. This generates vapor in the vapor generation region of the air path. Liquid that is vaporized from the liquid transport element is replaced by more liquid drawn from the reservoir by capillary action. While the vaporizer 40 is activated, a user inhales on the mouthpiece end 52 of the cartridge. This causes air to be drawn through whichever control unit air inlet 14 aligns with the air inlet 50 of the cartridge (which will depend on the orientation in which the cartridge was inserted into the control unit receptacle 8). Air then enters the cartridge through the air inlet 50, passes along the gap 76 in the double-walled section 74 of the housing part 32, passes between the resilient plug 44 and the end cap 48 before entering the vapor generation region surrounding the vaporizer 40 through the hole 106 in the base part 100 of the resilient plug 44. The incoming air mixes with vapor generated from the vaporizer 40 to form a condensation aerosol, which is then drawn along the outlet tube 38 and the housing part inner 62 before exiting through the mouthpiece outlet/vapor outlet 60 for user inhalation.

Thus in accordance with certain embodiments of the disclosure, a cartridge for a vapor provision system may generally comprise a housing part having a mouthpiece end and an interface end, wherein the mouthpiece end includes a vapor outlet for the cartridge and the interface end includes an interface for coupling the cartridge to a control unit. An air channel wall (which may be formed by various components of the cartridge) extends from an air inlet for the cartridge to the vapor outlet via a vapor generation region in the vicinity of a vaporizer. The cartridge has a reservoir within the housing part containing liquid for vaporization. The reservoir is defined by a region within the housing part which is outside the air channel 65 and an end of the reservoir at the interface end of the housing part is sealed by a resilient plug comprising a base part and an outer wall, wherein the outer wall of the resilient plug forms a seal with an inner surface of the housing part. Respective ends of a liquid transport element pass through opening in the air channel 65 or into the reservoir so as to convey liquid from the reservoir to the vaporizer.

One aspect of some particular cartridge configurations in accordance with certain embodiments of the disclosure is the manner in which the resilient plug 44 provides a seal to the housing part 32. In particular, in accordance with some example implementations the outer wall 102 of the resilient plug 44 which seals to the inner surface of the housing part 32 to form the end of the liquid reservoir extends in direction parallel to the longitudinal axis of the cartridge to a position which is further from the interface end of the cartridge than the liquid transport element/vaporizer. That is to say, the ends of the liquid transport element extends into the liquid reservoir in a region which is surrounded by the outer sealing wall of the resilient plug. Not only does this help seal the reservoir against leakage, it allows the geometry of the reservoir in the region which supplies the liquid transport element with liquid to be governed by the geometry of the resilient plug. For example, the radial thickness of the reservoir in this region can readily be made smaller than the radial thickness in other longitudinal positions along the air channel 65, which can help trap liquid in the vicinity of the liquid transport element, thereby helping to reduce the risk of dry out for different orientations of the cartridge during use.

The outer wall of the resilient plug may, for example, contact the inner surface of the housing part at locations over a distance of at least 5 mm, 6 mm, 7 mm, 8 mm, 9 mm and 10 mm in a direction extending from the interface end to the mouthpiece end (i.e. parallel to the longitudinal axis). The outer wall of the resilient plug may be in contact with the inner surface of the housing over the majority of this distance, or the outer wall of the resilient plug may include a number of (e.g. four) circumferential ridges 140 to help improve sealing. The resilient plug may be slightly oversized relative to the opening in the housing part so that it is biased into slight compression. For example, for the implementation shown in FIG. 3B, the interior width of the housing part into which the resilient plug is inserted in the plane of this figure is around 17.5 mm, whereas the corresponding width of the resilient plug is around 18 mm, thereby placing the resilient plug into compression when inserted into the housing part. As can be most readily seen in FIGS. 5A to 5C, whereas the outer cross section of the cartridge housing part is symmetric under a 180° rotation, the resilient plug 44 does not have the same symmetry because it includes a flat 142 on one side to accommodate the air channel gap 76 provided by the double-walled section 74 of the housing part (i.e. the resilient plug is asymmetric in a plane perpendicular to a longitudinal axis of the cartridge to accommodate the double-walled section of the housing part).

In terms of the radial size/width of the reservoir in the annular region where the liquid transport element extends into the reservoir, a distance between the air channel wall and the outer wall of the resilient plug in this region may, for example, be in the range 3 mm to 8 mm. In the example cartridge discussed above which has a generally oval housing part and a generally circular air channel 65, it will be appreciated the thickness of the reservoir is different at different locations around the air channel 65. In this example the liquid transport element is arranged to extend into the reservoir in the region where it is widest in the axial direction, i.e. into the "lobes" of the oval reservoir around the air channel 65. The portions of the liquid transport element that extend into the reservoir may, for example, have a length, as measured from the interior of the air channel wall, in the range 2 mm to 8 mm, e.g. in the range 3 mm to 7 mm or in the range 4 mm to 6 mm. The specific geometry in this regard (and for other aspects of the configuration) may be chosen having regard to a desired rate of liquid transport, for example having regard to the capillary strength of the liquid transport element and the viscosity of the liquid, and may be established for a given cartridge design through modelling or empirical testing.

Another aspect of some particular cartridge configurations in accordance with certain embodiments of the disclosure is the manner in which the air channel 65 is routed through the cartridge, and in particular from the air inlet to the vicinity of the vaporizer (the vapor generation region). In particular, whereas in a conventional cartridges an air inlet is typically provided at the interface end of the cartridge, in accordance with certain embodiments of the disclosure, an air inlet for the cartridge is located in a side wall of the housing part at a position which is further from the interface end than at least a part of the resilient plug that seals an end of the reservoir. Thus, the air channel 65 in the cartridge is initially routed from the air inlet towards the interface end and bypasses the resilient plug before changing direction and entering the vapor generation chamber through the resilient plug. This can allow the outer surface of the cartridge at the interface end, where it is closest to the vaporizer, to be closed, thereby helping to reduce the risk of leakage from the cartridge, both in terms of liquid coming through the openings in the air channel 65 which is not retained by the liquid transport element in the air channel 65 (e.g. due to saturation/agitation) or liquid that has being vaporized but condensed back to liquid in the air channel 65 during use. In some implementations, a distance from air inlet to the interface end of the housing part may be at least 5 mm, 6 mm, 7 mm, 8 mm, 9 mm or 10 mm.

In some example implementations an absorbent element, for example a portion of sponge material or a series of channels forming a capillary trap, may be provided between the air inlet and the vapor generation chamber, for example in the region air channel 65 formed between the base of the resilient plug and the end cap, to further help reduce the risk of leakage by absorbing liquid that forms in the air channel 65 and so helping prevent the liquid travelling around the air channel 65 through the air inlet or towards the vapor outlet.

In some example implementations the air channel 65 from the air inlet to the vapor outlet may have its smallest cross-sectional area where it passes through the hole 106 in the resilient plug. That is to say, the hole in the resilient plug may be primarily responsible for governing the overall resistance to draw for the electronic cigarette.

Another aspect of some particular cartridge configurations in accordance with certain embodiments of the disclosure is the manner in which the dividing wall element divides the air reservoir into two regions, namely a main region above the dividing wall (i.e. towards a mouthpiece end of the cartridge) and a liquid-supply region below the dividing wall (i.e. on the same side of the dividing wall as where the liquid transport element extends from the vaporizer into the reservoir). The dividing wall includes openings to govern the flow of liquid on the main region to the liquid supply region. The dividing wall can help retain liquid in the liquid supply region of the reservoir, example when the electronic cigarette is tilted through various orientations, which can help avoid dry out. The dividing wall can also conveniently provide a mechanical stop for the resilient plug to abut/press against so as to help correctly locate the resilient plug during assembly and maintain the resilient plug in slight compression between the dividing wall and the end cap when the cartridge is assembled.

In the example discussed above, the dividing wall is formed as a separate element form the housing part, wherein an inner surface of the housing part includes one or more protrusions arranged to contact the side of the dividing wall facing the mouthpiece end of the cartridge to locate the dividing wall along a longitudinal axis of the cartridge, but in other examples the dividing wall may be integrally formed with the housing part.

In the example discussed above the dividing wall is in the form of an annular band around the air channel 65 and comprises four fluid communication openings 150 located in respective quadrants of the band. However, more or fewer openings through the dividing wall may be provided in different implementations. Individual openings may, for example, have an area of between 4 mm$^2$ and 15 mm$^2$.

A combined area for the at least one openings as a fraction of the total area of the dividing wall exposed to liquid supply region of the reservoir region may be, for example, from 20% to 80%; 30% to 70% or 40% to 60%.

It will be appreciated that while the above description has focused on some specific cartridge configurations comprising a number of different features, cartridges in accordance with other embodiments of the disclosure may not include all these features. For example, in some implementations an air path generally of the kind discussed above, i.e. with an air inlet which is in a sidewall of the cartridge and closer to the mouthpiece end of the cartridge than the vaporizer, may be provided in a cartridge which does not include a resilient plug with an outer sealing wall which extends around the vaporizer and/or does not include a dividing wall element of the kind discussed above. Similarly, a cartridge which does include a resilient plug with an outer sealing wall which extends around the vaporizer may have an air inlet into the cartridge which is at the interface end of the cartridge, and not in a sidewall, and which may also not have a dividing wall element of the kind discussed above. Furthermore, a cartridge which does include a dividing wall element, might not include an air inlet located further from the interface end of the cartridge than the vaporizer and/or an extended outer sealing wall for a resilient plug as discussed above.

Thus, there has been described a cartridge for a vapor provision system comprising the cartridge and a control unit, wherein the cartridge comprises: a housing part having a mouthpiece end and an interface end, wherein the mouthpiece end includes a vapor outlet for the cartridge and the interface end includes an interface for coupling the cartridge to the control unit; an air channel 65 extending from an air inlet for the cartridge to the vapor outlet, wherein the air channel 65 is defined by an air channel wall; a reservoir within the housing part for liquid for vaporization, wherein an end of the reservoir at the interface end of the housing part is sealed by a resilient plug comprising a base part and an outer wall extending away from the base part towards the mouthpiece end of the housing part, wherein the outer wall of the resilient plug forms a seal with an inner wall of the housing part; a vaporizer for vaporizing liquid from the reservoir to generate vapor in a vapor generation region of the air channel 65 for user inhalation; and a liquid transport element for transporting liquid from the reservoir to the vaporizer through an opening in the air channel wall, wherein the opening in the air channel wall is located nearer to the base part of the resilient plug than the top of the outer wall of the resilient plug so that a portion of the liquid transport element extends into the reservoir in a region surrounded by the outer wall of the resilient plug.

There has also been described a cartridge for a vapor provision system comprising the cartridge and a control unit, wherein the cartridge comprises: a housing part having a mouthpiece end and an interface end connected by a side wall, wherein the mouthpiece end includes a vapor outlet for the cartridge and the interface end includes an interface for coupling the cartridge to a control unit; an air channel 65 extending from an air inlet for the cartridge to the vapor outlet; a reservoir within the housing part containing liquid for vaporization, wherein an end of the reservoir at the interface end of the housing part is sealed by a resilient plug, and wherein an outer wall of the resilient plug forms a seal with an inner surface of the housing part; a vaporizer for vaporizing liquid from the reservoir to generate vapor in a vapor generation region of the air channel 65; and a liquid transport element for transporting liquid from the reservoir to the vaporizer; wherein the air inlet for the cartridge is located in the side wall of the housing part at a position which is further from the interface end than at least a part of the resilient plug.

There has also been described a cartridge for a vapor provision system comprising the cartridge and a control unit, wherein the cartridge comprises: a housing part having a mouthpiece end and an interface end, wherein the mouthpiece end includes a vapor outlet for the cartridge and the interface end includes an interface for coupling the cartridge to a control unit; an air channel 65 extending from an air inlet in the housing part to the vapor outlet; a reservoir within the housing part containing liquid for vaporization vapor, wherein an end of the reservoir at the interface end of the housing part is sealed by a resilient plug, wherein the reservoir includes a dividing wall between a first reservoir region on a side of the dividing wall facing the mouth piece end of the housing part and a second reservoir region on a side of the dividing wall facing the interface end of the housing part, wherein the dividing wall comprises at least one fluid communication opening to provide fluid communication between the first reservoir region and the second reservoir region; and a liquid transport element arranged to transport liquid from the second region of the reservoir to a vaporizer for generating vapor in a vapor generation region for user inhalation.

While the above described embodiments have in some respects focused on some specific example vapor provision systems, it will be appreciated the same principles can be applied for vapor provision systems using other technologies. That is to say, the specific manner in which various aspects of the vapor provision system function, for example in terms of the underlying form of the vaporizer or vaporizer technology used are not directly relevant to the principles underlying the examples described herein.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention (s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. A cartridge for a vapor provision system comprising the cartridge and a control unit, wherein the cartridge comprises:
   a housing part having a mouthpiece end and an interface end, wherein the mouthpiece end includes a vapor outlet for the cartridge and the interface end includes an interface for coupling the cartridge to the control unit;
   an air channel extending from an air inlet in the housing part to the vapor outlet;
   a reservoir within the housing part containing liquid for vaporization, wherein an end of the reservoir at the interface end of the housing part is sealed by a resilient plug, wherein the reservoir includes a dividing wall between a first reservoir region on a side of the dividing wall facing the mouthpiece end of the housing part and a second reservoir region on a side of the dividing wall facing the interface end of the housing part, wherein the dividing wall comprises at least one fluid communication opening to provide fluid communication between the first reservoir region and the second reservoir region, and wherein the dividing wall is positioned in the cartridge to provide a stop for the resilient plug such that the resilient plug abuts the dividing wall; and
   a liquid transport element arranged to transport liquid from the second reservoir region of the reservoir to a vaporizer for generating vapor in a vapor generation region for user inhalation.

2. The cartridge of claim 1, wherein the resilient plug comprises a base part and an outer wall extending away from the base part towards the mouthpiece end of the housing part, wherein a top surface the outer wall abuts a peripheral part of the dividing wall.

3. The cartridge of claim 1, wherein the dividing wall is formed as a separate element from the housing part, and wherein an inner surface of the housing part includes one or more protrusions arranged to contact the side of the dividing wall facing the mouthpiece end of the cartridge to locate the dividing wall along a longitudinal axis of the cartridge.

4. The cartridge of claim 1, wherein the air channel passes through an air channel opening in the dividing wall.

5. The cartridge of claim 1, wherein the dividing wall includes one or more projections extending away from a plane of the dividing wall towards the interface end of the cartridge which engage with one or more corresponding recesses in the resilient plug.

6. The cartridge of claim 1, wherein the dividing wall includes one or more projections extending away from a plane of the dividing wall towards the interface end of the cartridge which engage with respective cradles formed in the resilient plug to define a liquid transport element opening through which the liquid transport element passes.

7. The cartridge of claim 1, wherein a combined area of the at least one fluid communication opening comprises a fraction of a total area of the dividing wall exposed to the second reservoir region within a range of 20% to 80%.

8. The cartridge of claim 1, wherein the at least one fluid communication opening has an area of between 4 $mm^2$ and 15 $mm^2$.

9. The cartridge of claim 1, wherein the dividing wall is a band around the air channel and comprises four fluid communication openings located in respective quadrants of the band.

10. The cartridge of claim 1, wherein the liquid transport element comprises a capillary wick.

11. The cartridge of claim 1, wherein the vaporizer comprises a heater.

12. The cartridge of claim 1, wherein the liquid transport element and the vaporizer comprise a single integrated element.

13. A vapor provision system comprising the cartridge of claim 1 and a control unit, wherein the control unit comprises a cartridge receiving section that includes an interface arranged to cooperatively engage with the interface end of the cartridge so as to releasably couple the cartridge to the control unit, wherein the control unit further comprises a power supply and control circuitry configured to selectively supply power from the power supply to the vaporizer in the cartridge via the cooperatively engaging interfaces.

14. Cartridge means for vapor provision system means comprising the cartridge means and a control unit means, the cartridge means comprising:
   a housing part means having a mouthpiece end means and an interface end means, wherein the mouthpiece end means includes a vapor outlet means for the cartridge means and the interface end means includes an interface means for coupling the cartridge means to the control unit means;
   an air channel means extending from an air inlet means in the housing part means to the vapor outlet means;
   a reservoir means within the housing part means containing liquid for vaporization, wherein an end of the reservoir means at the interface end means of the housing part means is sealed by a resilient plug means, wherein the reservoir means includes a dividing wall means between a first reservoir region on a side of the dividing wall means facing the mouthpiece end means of the housing part means and a second reservoir region on a side of the dividing wall means facing the interface end means of the housing part means, wherein the dividing wall means comprises at least one fluid communication opening means to provide fluid communication between the first reservoir region and the second reservoir region, and wherein the dividing wall means is positioned in the cartridge means to provide a stop means for the resilient plug means such that the resilient plug means abuts the dividing wall means; and a liquid transport element means arranged to transport liquid from the second reservoir region means to a vaporizer means for generating vapor in a vapor generation region for user inhalation.

\* \* \* \* \*